United States Patent [19]

Anapliotis et al.

[11] Patent Number: 5,156,142
[45] Date of Patent: Oct. 20, 1992

[54] ENDOSCOPE

[75] Inventors: Emmanuel Anapliotis, Berlin; Gisbert Schich, Ansbach, both of Fed. Rep. of Germany

[73] Assignee: Effner GmbH, Berlin, Fed. Rep. of Germany

[21] Appl. No.: 602,297
[22] PCT Filed: Nov. 19, 1989
[86] PCT No.: PCT/DE89/00729
  § 371 Date: Nov. 21, 1990
  § 102(e) Date: Nov. 21, 1990
[87] PCT Pub. No.: WO90/05480
  PCT Pub. Date: May 31, 1990

[30] Foreign Application Priority Data

Nov. 18, 1988 [DE] Fed. Rep. of Germany ... 8814573[U]

[51] Int. Cl.⁵ .............................................. A61B 1/06
[52] U.S. Cl. ......................................... 128/6; 128/4
[58] Field of Search ................................... 128/4, 6

[56] References Cited

U.S. PATENT DOCUMENTS

| 3,261,349 | 7/1966 | Wallace | 128/6 |
| 3,261,351 | 7/1966 | Wallace | 128/6 |
| 3,261,356 | 7/1966 | Wallace | 128/6 |
| 3,297,022 | 1/1967 | Wallace . | |
| 4,063,796 | 12/1977 | Hiltebrandt | 128/4 |
| 4,369,768 | 1/1983 | Vukovic . | |
| 4,606,331 | 8/1986 | Shene | 128/4 |
| 4,819,620 | 4/1989 | Okutsu | 128/6 |
| 4,905,082 | 2/1990 | Nishigahi et al. | 128/6 |
| 4,973,321 | 11/1990 | Michelson | 128/4 |

FOREIGN PATENT DOCUMENTS

| 1696900 | 8/1954 | Fed. Rep. of Germany . |
| 1117256 | 11/1961 | Fed. Rep. of Germany . |
| 3727190 | 2/1988 | Fed. Rep. of Germany . |
| 3504252 | 10/1988 | Fed. Rep. of Germany . |
| 1311018 | 3/1973 | United Kingdom . |

Primary Examiner—Gene Mancene
Assistant Examiner—Frank A. LaViola
Attorney, Agent, or Firm—Spencer, Frank & Schneider

[57] ABSTRACT

An endoscope, in particular an athroscope, comprising a shaft carrying an optical unit and optical fibers arranged concentrically around the shaft, in which the shaft (5) carrying the optical unit is part of an observation component (1) and the optical fibers (14) are part of an illumination component (2), whereby the illumination component (2) comprises a double-walled sheath made of two hollow cylinders and the optical fibers (14) pass between the walls (15a and 15b) formed by the hollow cylinders and the observation component (1) can be inserted into the illumination component (2).

9 Claims, 2 Drawing Sheets

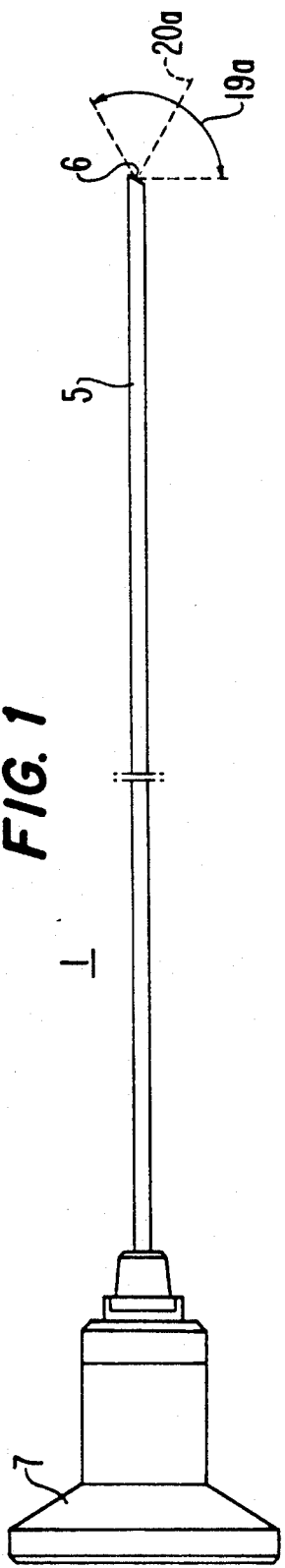
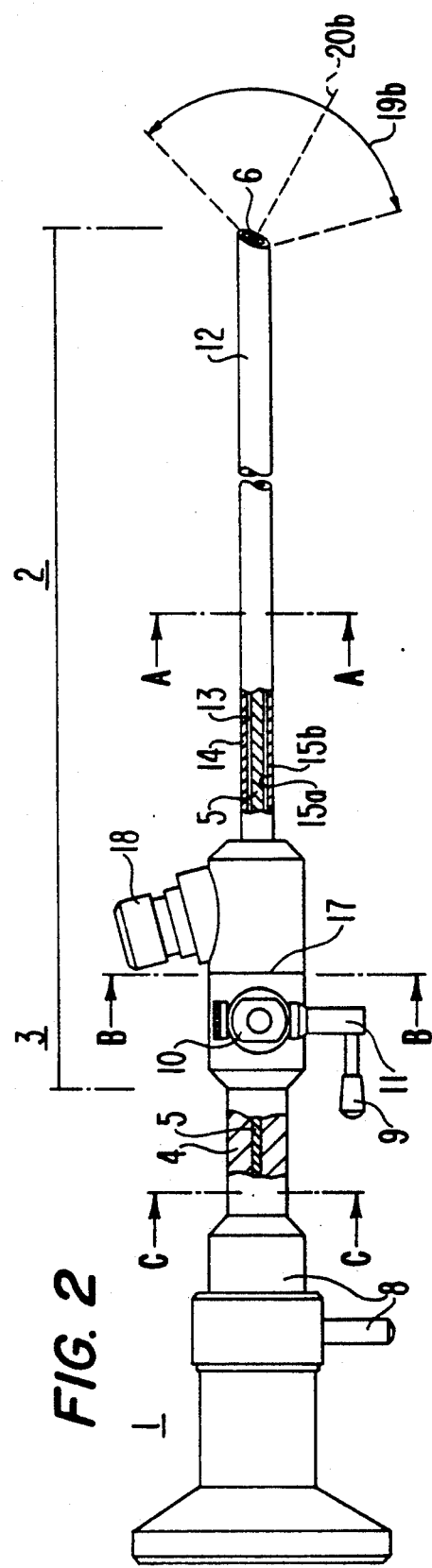
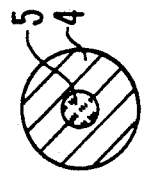
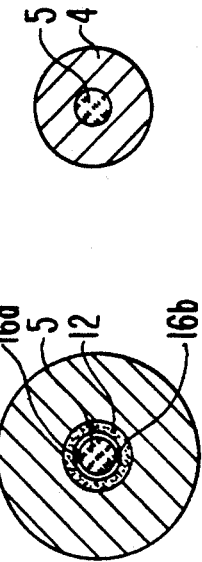
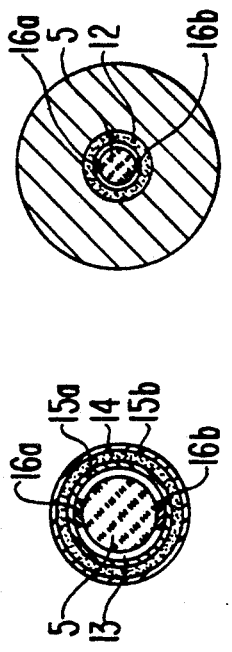

ENDOSCOPE

BACKGROUND OF THE INVENTION

The invention relates to an endoscope including a shaft carrying an optical arrangement with optical fibers arranged concentrically around the shaft.

Such endoscopes are used, in particular in the form of athroscopes, to examine and treat acute articular joint spaces, and mainly those of the knee joint. Athroscopy is a preferred and often implemented method to examine meniscus injuries.

Very often endoscopes combined with surgical instruments are not only used to observe but also to illuminate the surgery area. Endoscopes must therefore not only have superb optical parameters but must also possess excellent cold light illumination of high intensity as their distinguishing features.

The crowded construction of the endoscopes known in the art is disadvantageous as it means that only relatively small cross-sections of the optical means and the optical fibers can be chosen, in particular when irrigation channels are combined with the shaft of the endoscope.

Furthermore disadvantageous with the endoscopes known in the art is that the observation and illumination components are fixed together. In the case of the optical means of the endoscope being damaged—which can often occur during surgery—either the whole unit must be replaced or repaired. Such repairs are relatively costly and time-consuming due to the necessary but complicated disassembly involved.

Due to the development trend towards higher performance and more expensive instruments with a narrow specialized field of application the repair work can only be carried out by specialized workshops, so that the repair costs also increase continually. Often the extensive and costly maintenance work can only be carried out by the manufacturers maintenance specialists.

SUMMARY OF THE INVENTION

The object of this invention is to eliminate the above-mentioned disadvantages of the endoscopes described above and to aim at providing an endoscope with a greater availability due to a simplification of the repair and maintenance work required.

The above and other objects are accomplished in accordance with the invention by the provision of an endoscope including: an observation component including a shaft having a proximal end, a distal end and an interior, and optical means disposed in the interior of the shaft for observing from the proximal end an object area adjacent the distal end of the shaft; an illumination component including an outer hollow cylinder, an inner hollow cylinder concentrically arranged with the outer cylinder to define a first space therebetween, and optical fibers extending longitudinally within the first space for transmitting light to illuminate the object area, the observation component being removably inserted in the inner hollow cylinder with a second space being defined between the shaft of the observation component and the inner hollow cylinder; and guidance bars extending longitudinally within the second space for guiding the shaft of the observation component and forming within the second space a suction channel and an irrigation channel separated by the guidance bars.

The invention is based on the realization that endoscopes usually consist of a combination of two different functional components, namely an observation component and an illumination component. Far-reaching consequences for the servicibility and the scope of utilization can be obtained due to the two components being separable from one another. As the separation is carried out by the two components being displaced relative to one another this can also be carried out in the operating theatre so that the observation component can be replaced immediately in the case of a defect. The cylindrical observation component can easily be pulled out of the hollow cylindrical illumination component. In this way it is possible to repair or inspect each of the components separately. In addition, numerous combinations of differently shaped observation components with differing illumination components are possible.

According to an advantageous feature of the invention the endoscope comprises a space for the through-flow of irrigation or suction liquids or gases situated between the shaft of the observation component carrying the optical means and the double-walled hollow cylinder of the illumination component which can hold the optical fibers. In contrast to the endoscopes or athroscopes known in the art not the suction pip but the double-walled hollow cylinder which holds the optical fibers forms the outer edge of the tube-like shaft of the athroscope. Due to this, a ringlike region of a greater diameter is available to hold the optical fibers and a greater number of optical fibers can be passed through the region. The illumination intensity can therefore be substantially increased.

Athroscopes usually comprise an endoscope with an optical fiber illumination component in conjunction with a suction or an irrigation device or in conjunction with a combined suction and irrigation device. The endoscope is used to observe the articular joint spaces. A gas, for example, can be injected using the irrigation device in order to extend the articular joint space.

As the suction and irrigation channels do not have to be pushed onto the endoscope separately, but are "integrated" in the endoscope shaft between the observation and the illumination components, the wall cross-section is reduced, which not only enables the cross-section of the observation component but also that of the illumination component to be increased. With this, for example, the diameter of the observation channel (lens diameter) can be increased from 2,7 to 3,0 mm. As the achievable optical resolution increases with the square of the aperture, which itself is linearly dependent on the lens diameter, the achievable improvement is considerable.

A socket for connecting the optical fiber illumination device to the light source is disposed at the distal end of the portion of the arthroscope which is inserted into the articular joint space. Special valve-like locking means for the suction and/or irrigation mechanism can be connected directly above the socket or separated by a spacer tube by locking or screwing in. A thereto adjoining guidance tube enables an exactly centered insertion of the observation component of the endoscope and acts to effectively protect the shaft carrying the optical means from mechanical overstressing or from damage due to other instruments. The side nearest the eyepiece of the observation component can be locked onto the guidance tube.

In the inserted position the shaft carrying the optical means of the observation component and the double-walled hollow cylindrical sheath for the optical fibers of the illumination component are essentially of the same distal length. A reduction of the optical field of vision can thus be avoided.

In order to avoid tissue damage during the insertion of the endoscope its distal end is preferably rounded in shape when viewed together with the convex form of the front lens on the side nearest the object.

By opening the locking device between the observation component and the guidance tube and by partially withdrawing the observation component it is quite easily possible to rinse the objective of the observation component in order to dispose of eventual contaminants. This in itself is an already known method but acts much more effectively with the components and the construction of the endoscope according to the invention than with those known to the art as the irrigation or suction fluid is rinsed directly around the objective. In addition, the inner wall of the suction/irrigation channel is formed directly by the shaft carrying the optical means.

The viewing angle, for example 90° (wide angle optics) and the direction of view, for example 0°, 30° or 70° with respect to the longitudinal axis of the athroscope can also be freely chosen during surgery due to the quick and easy exchangeability of the observation component. By turning the observation component inside the guidance tube and with a direction of view not equal to 0° an overview of the surrounding areas of the surgical area can be obtained. The chosen observation component is chosen according to the required illuminated area of the object region.

BRIEF DESCRIPTION OF THE DRAWINGS

The invention will be described in greater detail below together with a description of the preferred embodiment of the invention as shown in the drawings. They show:

FIG. 1 an advantageous embodiment of the component as a part of the endoscope in accordance with the present invention, FIG. 2 the endoscope of this invention in the embodiment as an athroscope in the assembled condition—partially shown as a sectional view, FIG. 3 an enlargened sectional view taken in the direction of lines A—A of FIG. 2, FIG. 4 an enlargened sectional view taken in the direction of lines B—B of FIG. 2, FIG. 5 an enlargened sectional view taken in the direction of lines C—C of FIG. 2 and FIG. 6 a perspective view of a further embodiment of the endoscope in accordance with the present invention.

DETAILED DESCRIPTION OF THE PREFERRED EMBODIMENT

Figure 6:
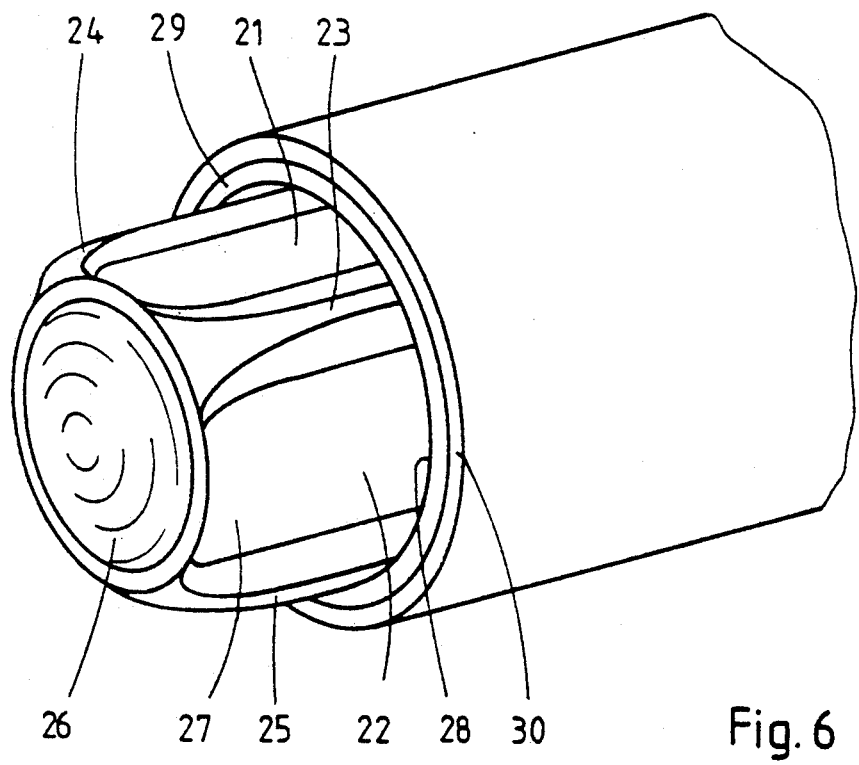

The following description refers both to FIGS. 1 and 2, whereby FIG. 2 shows the complete endoscope and FIG. 1 only shows the observation component which has been removed from the illumination component.

The endoscope according to the invention in an embodiment as an athroscope comprises an observation component 1, an illumination component 2, a component 3 comprising a connection or connections for the suction or/and irrigation devices and a guidance tube 4. All of the major components 1 to 4 of the athroscope can be very differently shaped for various uses. A plurality of combinations can be realized by way of the connection points, which will be described below.

The observation component 1 comprises a shaft 5 carrying optical means, an objective 6 at the distal end of the shaft 5, an eyepiece 7 and connection elements 8 at the end of the shaft 5 nearest the eyepiece 7. The connection elements 8 enable the observation component 1 to be clamped to the guidance tube 4. The guidance tube 4 serves to center the inserted rod shaped shaft 5 and to protect the shaft 5 from mechanical damage. At its other end, the guidance tube 4 is connected to the in or/and outflow of the component 3 regulating the suction or irrigation medium of the suction or irrigation device. The component 3 enables the inflow or outflow of fluids or gases via at least one hollow connecting tube 11, which is situated radially to the longitudinal axis of the arthroscope, by way of a lever 9 which opens a valve-like locking device 10.

A tube can be connected to the connecting tube 11 which enables the in- or outflow of the fluids or liquids. The suction or irrigation media inside the cannula 12, which is to be inserted into the articular joint space flows in a hollow tube 13, which is ring-like in cross-section. The inner wall of the hollow tube 13 is formed by the cylindrical shaft 5 of the observation component 1 and the outer wall also acts as the inner limit of a double-walled hollow cylinder, which carries the optical fibers 14 and which consists of an inner wall 15a and an outer wall 15b, whereby the outer wall 15b also forms the outer limit of the cannula 12 which is to be inserted into the articular joint space. The inner wall 15a of the illumination channel can comprise two longitudinal bars 16a and 16b which are preferably oppositely disposed from one another (FIG. 3). The longitudinal bars 16a and 16b act as spacers between the shaft carrying the optical means 5 and the inner wall 15a of the double-walled hollow cylinder carrying the optical fibers 14 and separate the hollow tube 13 into two separate chambers with preferably same sized ring segment shaped cross-sections, so that a number of fluid or gas streams can be completely separated from one another.

The double-walled hollow cylinder 15a/15b is connected at a connection point 17 to the side of component 3 which faces the distal end of the athroscope and which comprises the locking device 10 for the suction-/irrigation device.

The cross-section at the connection point 17 is shown in FIG. 4. The valve-like locking device 10 which regulates the in or/and outflow of substances and which is part of the component 3 of the suction or/and irrigation device is situated behind the component comprising a light source connecting piece 18 if viewed from the distal end of the athroscope. The light source connecting piece 18 stands out radially from the longitudinal axis of the athroscope and serves as a connection for self-supporting or non self-supporting (flexible) optical fibres cables.

Apart from enabling the connection of various components 3 comprising valve-like locking devices the connection point 17 also enables the direct connection of a guidance tube 4 to the component comprising the light source connecting piece 18. The hollow tube 13 which forms the suction or/and irrigation channel remains unused in this case. FIG. 5 shows a cross-section through a guidance tube.

The length of the guidance tube is such that the distal end of the observation component 1 approximately corresponds with the distal end of the illumination component 2 if the observation component 1 is inserted fully to the stop. In this manner, on condition that the observation component 1 is paired with the illumination component 2 such that the viewing angle 19a and the direction of view 20a of the observation component corresponds with the viewing angle 19b and the direction of view 20b of the illumination component 2, it can be guaranteed that the illuminated object area is practically identical with the object area to be observed. In order to be able to set the fixed correspondence easily and quickly with respect to the viewing angle and the direction of view, the observation component 1 can be clamped at the set angle position relative to the illumination component 2 using connection elements 8.

To rinse the objective 6 the clamping of the observation component 1 using the connection elements 8 can be loosened so that the observation component can be partially withdrawn. By loosening the connection elements 8 an "allround view" can be achieved due to the rotatability of the observation component 1 in the guidance tube 4 if an observation component 1 is used with a direction of view which differs from the longitudinal axis of the athroscope.

FIG. 6 shows a perspective view of the distal end of an endoscope which is a variation of the embodiment shown in FIG. 3. It comprises two fluid or gas channels 21 and 22, which are separated from one another by longitudinal bars 23 to 25 or from another channel which is not shown in the drawing.

The longitudinal bars 23 and 24 taper in the radial direction and become wider in the direction of the distal end. In a longitudinal cross-section the bars are rounded off to such an extent that their dimensions decrease at the distal end in the radial direction.

The shown embodiment therefore comprises a completely rounded tip whose outer contours are also completely rounded in the direction of the distal end, which enables an easy, non tissue-damaging, and hook-free insertion of the endoscope optical means.

The curvature of the objective lens 26 arched convexly on the object side goes continually over into the curvature of the shaft 27 carrying the optical means, into the inner wall 28, into a light emittance surface of the optical fibers 29 and into an outer wall 30, on condition that the observation component is inserted as far as the stop into the illumination component comprising the inner wall 28, the optical fibers 29 and the outer wall 30. Due to the widening of the bars in the base region the rounded shape can work in an advantageous manner against being hooked during insertion. The bars are limited in their dimensions in the radial direction such that they do not hinder the displacement of the shaft carrying the optical means relative to the illumination component.

The unproblematic and quick replacability of the observation component 1, which can also be replaced during surgery has been proven to be particularly advantageous. For example, various optical means with differing apertures or with differing directions of view can be inserted in turn.

As the outer wall 15b of the illumination channel forms the outer limit of the cannula 12 and not—as is the case with the arthroscopes known in the art—the outer limit of the suction or irrigation channel, more optical fibers can be inserted which results in an appreciable increase in the illumination intensity.

The reduced wall thicknesses also allow for a considerable increase in the diameter of the shaft carrying the optical means and therefore also allow for a considerable increase in the clear diameter of the objective 6.

The increase in height of the aperture obtained in this manner leads to a great improvement in the resolution capacity.

The present invention is not limited in its embodiment to the above-described preferred embodiment. Rather, a number of variations are conceivable which take advantage of the described solution even for basically different configurations.

We claim:

1. An endoscope, comprising:
   an observation component including a hollow shaft having a proximal end, a distal end and an interior, and optical means disposed in the interior of said shaft for observing from the proximal end an object area adjacent the distal end of said shaft;
   an illumination component including an outer hollow cylinder, an inner hollow cylinder concentrically arranged with said outer cylinder to define a first space there between, and optical fibers extending longitudinally within the first space for illuminating the object area, said observation component being removably inserted in said inner hollow cylinder with a second space being defined between the shaft of said observation component and said inner hollow cylinder; and
   guidance bars extending longitudinally within the second space for guiding the shaft of said observation component and forming within the second space a suction channel and an irrigation channel separated by said guidance bars.

2. An endoscope as defined in claim 1, said illumination component has a distal end which, when said observation component is fully inserted in said illumination component, approximately corresponds in position, within a few millimeters, with the distal end of the shaft of said observation component.

3. An endoscope as defined in claim 1, wherein said guidance bars center the distal end of the shaft of said observation component within said illumination component and said guidance bars are tapered in a radial direction and are rounded off at the distal end of said shaft.

4. An endoscope as defined in claim 1, wherein said illumination component has a distal end presenting a direction of illumination and an angle of illumination, and said optical means has a direction of view and an angle of view at the distal end of said shaft which corresponds, respectively, with the direction of illumination and the angle of illumination of said observation component.

5. An endoscope as defined in claim 1, wherein said observation component and said illumination component are rotatable relative to one another.

6. An endoscope as defined in claim 5, including means for fixing said observation component and said illumination components so that they do not rotate relative to one another.

7. An endoscope as defined in claim 1, wherein said optical fibers are glass optical fibers.

8. An endoscope as defined in claim 1, further comprising light source connection means for connecting a light source to said optical fibers and suction and irrigation connection means, disposed behind said light source connection means when viewed from the distal end of said shaft, for selectively connecting said suction channel to a source of suction and said irrigation channel to an irrigation medium.

9. An endoscope as defined in claim 1, wherein said suction and irrigation connection means comprises a component which is removably connected in a coaxial manner to said illumination component and has a first side facing said illumination component that includes an aperture corresponding to said suction and irrigation channels and means forming an outwardly tight closure, and a second side opposite said first side comprising only an aperture for receiving the shaft of said observation component.

* * * * *